United States Patent [19]

Brownell

[11] 4,270,778

[45] Jun. 2, 1981

[54] TUBE CONNECTOR WITH SECURITY MEANS

[75] Inventor: Richard G. Brownell, Greenwich, N.Y.

[73] Assignee: Sherwood Medical Industries Inc., St. Louis, Mo.

[21] Appl. No.: 35,864

[22] Filed: May 3, 1979

[51] Int. Cl.³ .............................................. F16L 37/12
[52] U.S. Cl. ................................. 285/305; 128/207.14; 128/247; 285/155; 285/332; 285/420; 285/423
[58] Field of Search ................... 285/305, 364, 114, 8, 285/260, 406, 332, 320, DIG. 2, 423, 420, DIG 22, 119, 38, 955; 24/16 PB; 128/1 R, 214.4, 247, 348, 349, 207.14; 29/450

[56] References Cited

U.S. PATENT DOCUMENTS

| 2,526,754 | 10/1950 | Johnson et al. ............ 285/320 X |
| 2,638,096 | 5/1953 | Waldhaus ..................... 128/348 |
| 3,334,631 | 8/1967 | Stebleton ...................... 128/351 |
| 3,388,705 | 6/1968 | Grosshandler ............... 285/8 X |
| 3,616,799 | 11/1971 | Sparks .......................... 128/351 |
| 3,659,612 | 5/1972 | Shiley et al. ................. 128/351 |
| 3,953,060 | 4/1976 | Eross ............................ 285/305 |
| 4,045,058 | 8/1977 | Eross ............................ 128/247 |
| 4,112,988 | 9/1978 | Nelson .......................... 24/16 PB |

FOREIGN PATENT DOCUMENTS

| 966982 | 5/1975 | Canada ........................ 24/16 PB |
| 496975 | 12/1938 | United Kingdom .......... 285/8 |

*Primary Examiner*—Dave W. Arola
*Attorney, Agent, or Firm*—Stanley N. Garber; William R. O'Meara

[57] ABSTRACT

A medical tube connecting device which includes a tube connector and a security connection member for connecting a medical tube, such as a tracheal tube, to a slip-fit coupling adapter of gas supply equipment. The connector has slip-fit couplers for connection with the adapter and the tube, and a flange with a pair of diametrically opposed slots extending inwardly from its outer periphery. The security member is an elastic strap having opposed end enlargements. The strap, in use, extends around a portion of the coupling adapter and the ends of the strap are received in the flange slots with the enlargements maintaining the strap in place.

3 Claims, 6 Drawing Figures

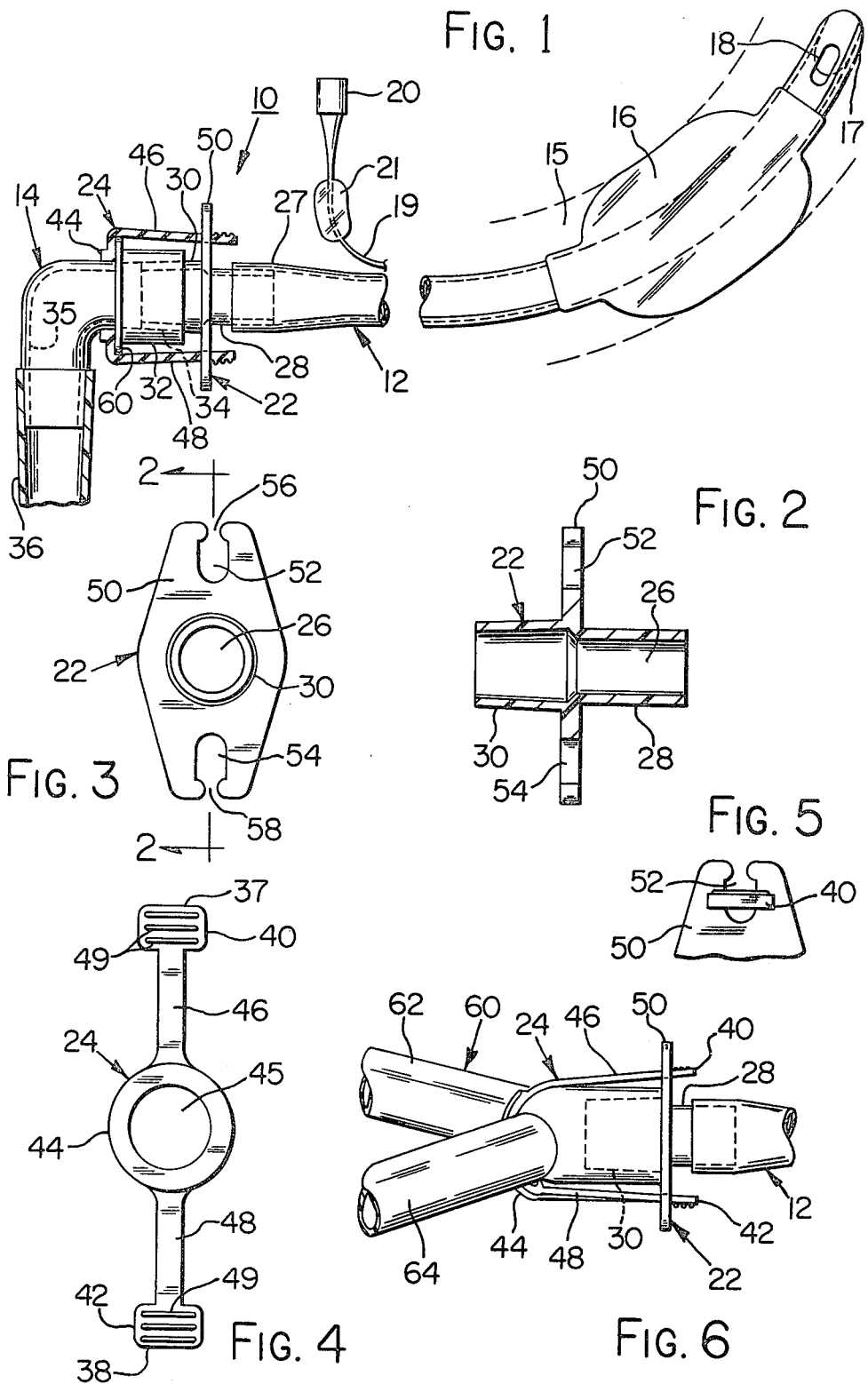

TUBE CONNECTOR WITH SECURITY MEANS

BACKGROUND OF THE INVENTION

This invention relates to medical tube connectors and, more particularly, to a medical tube connector with security means for connecting a medical tube to a fluid coupling of a gas supply apparatus.

Tracheal tubes, such as endotracheal or tracheostomy tubes, are generally provided with a tube connected at the proximal end which is connectible by a slip-fit connection to a standard 15 mm female fluid coupling or adapter of a gas supply system or circuitry. Such an arrangement is used, for example, to supply an anesthetic gas to a patient during surgery or to supply oxygen or a mixture of gases such as oxygen and air to the patient at other times, such as during post-surgery treatment.

The slip-fit between the connector and the equipment adapter permits a fluid-tight connection between the two, even where manufacturing tolerances, within limits, vary from one manufacturer to another. The slip-fit connection also allows easy and quick disconnection of the equipment from the tube when desired.

There is a danger, however, and especially where the tube is intended to remain intubated over a relatively long period of time, such as several hours, of the connector and adapter becoming inadvertently disconnected. Such disconnection could occur as a result of movement of the patient, equipment, or both. In order to avoid the danger of inadvertent separation, rubber bands are commonly wrapped around parts of the connector and adapter so that these parts are continuously resiliently urged toward each other so that limited movement of equipment or patient would not result in disconnection.

The use of conventional rubber bands to connect the tube connector with an adapter, even where one or both of these members are provided with rods or spikes for the rubber bands, is cumbersome, time consuming, and the rubber bands are subject to loss and breakage.

SUMMARY OF THE INVENTION

It is therefore an object of the present invention to provide an improved medical fluid connector for connecting a medical tube with a fluid coupling device which provides security means for preventing inadvertent disconnection of the two members and is relatively simple and effective in use.

In accordance with one form of the present invention, a medical tube connector device is provided which includes a tube connector and a security member. The connector has end portions respectively connectible with a tube and a fluid coupling. The security member is engageable with a part of the fluid coupling and has an end portion insertable in an opening in the connector and a part which engages the connector to prevent movement of the end portion from the opening.

These, as well as other objects and advantages of the present invention, will become apparent from the following detailed description and accompanying drawing.

BRIEF DESCRIPTION OF THE DRAWING

FIG. 1 is a side elevational view, partly in cross-section, of a medical connector device in accordance with a preferred embodiment of the invention connected between a tracheal tube and a fluid coupling of gas supply equipment;

FIG. 2 is an enlarged cross-sectional, side elevational view of the connector of FIG. 1;

FIG. 3 is a left side view of the connector of FIG. 2;

FIG. 4 is an enlarged plan view of the elastic security member of FIG. 1;

FIG. 5 is an enlarged fragmentary, right side view of the connector of FIG. 1; and FIG. 6 is a side elevational view showing the connector assembly and tube of FIG. 1 connected to a Y-coupling of gas supply apparatus.

DESCRIPTION OF THE PREFERRED EMBODIMENT

Referring now to the drawing, and more particularly to FIG. 1, a medical connector device, indicated generally at 10, is shown connecting a medical tube 12, such as a tracheal tube, to a fluid coupling or adapter 14. Adapter 14 is part of a pressurized gas supply system, such as an anesthetic gas, oxygen, or gas mixture supply system or circuit. The tube 12 is shown as an endotracheal tube disposed in the trachea 15 of a patient. Tube 12 is provided with a conventional inflatable cuff 16 shown sealing the trachea. The tube 12 is open at the distal end 17 and may be provided with an opening 18 extending through the tube sidewall to the tube lumen. The tube 12 is also conventionally provided with a secondary lumen (not shown) communicating with the cuff 16 and an external inflation tube 19 having a syringe tip coupling 20 containing a valve for selectively inflating and deflating the cuff. The inflation tube 19 may also be provided with a conventional pilot cuff 21 that is in fluid communication with cuff 16 for providing an external indication of the inflation condition of cuff 16. The tubes and cuffs may be formed of suitable plastics, for example, polyvinylchloride.

The connector device 10 includes a fluid connector 22 and a security member 24 which provides an elastic security or locking connection between the connector 22 and the adapter 14.

The connector 22, as seen also in FIGS. 2 and 3, is provided with a passage or bore 26 extending through it which transfers gas from the gas supply adapter 14 to the endotracheal tube 12. The connector may be formed by molding a suitable plastic such as polypropylene. The distal end portion of connector 22 is the form of an integral slip-fit connection member or coupler 28 shown in frictional, fluid-tight relation with the proximal end portion 27 to tube 12 in FIG. 1. The proximal end portion of connector 22 is also in the form of an integral slip-fit connection member or coupler which is indicated at 30. The coupler 30 is received within a female slip-fit coupling 32 at the distal end portion of adapter 14. The outer surface of coupler 30 is slightly tapered toward the proximal end of the connector so that it is capable of being manually forced into fluid-tight, frictional engagement with the inner walls 34 of the adapter coupling 32, even where there is a slight variation in the inner diameter of coupling 32 due to manufacturing tolerances. Because the adapter coupling 32 has been standardized in size as a 15 mm connector, the coupler 30 of the connector 22 will generally be sized to fit into such an adapter coupling.

While the coupling 32 of the adapter has been standardized in size, the adapters may otherwise vary in shape and construction, depending upon the equipment manufacturer and the type of gas supply system. For example, in some cases the adapter may include a rotatable fitting, or a swivel joint. Also, straight and right-angle adapters have been used. In FIG. 1, a single L-shaped or right-angle adapter having a through passage 35 is illustrated. The adapter is connected to a gas supply equipment hose 36.

The security member 24 of connector assembly 10, as seen also in FIG. 4, is formed of an elastic material such as a suitable soft, pliable, natural or synthetic, plastic or rubber-like material. One suitable elastic material is a thermoplastic elastomer known as Kraton-G (sold by Shell Chemical Company) which is a copolymer of polystyrene and polyethylenebutylene, and having a durometer of 55 on the Shore A scale. Connector 24 is shown as an elongated strap having opposed free ends 37 and 38 with enlargements 40 and 42, respectively, which serve as strap retaining abutments as will be described hereafter. At the longitudinal center of the security strap there is a closed loop portion 44 shown as a circular portion having an opening 45. Integrally connected at diametrically opposed portions of the circular portion 44 are straight strap portions or arms 46 and 48, respectively, which connect the circular portion 44 with the retaining abutments 40 and 42. The end abutments 40 and 42 are provided with a plurality of finger friction ridges 49 to aid in preventing slippage between the security member and fingers of the person stretching the member when put in use.

The connector 22 is provided with an integral flange 50 axially between the opposed integral slip-fit couplers 28 and 30 of the connector. Flange 50 has a pair of diametrically opposed slots 52 and 54 extending generally radially inwardly from the outer periphery of the flange for receiving the arms 46 and 48, respectively, of the security member 24 when in use. The slots have entrances 56 and 58, each having a width less than that of the radially inner portions of the slots and of the arms 46 and 48 of the security member 24 so that the arms will not inadvertently slip out of the slots after being inserted into the slots.

As seen in FIG. 1, the connector 22 is in frictional, fluid-tight connection with adapter 14 to connect the tube 12 in fluid communication with the adapter and gas supply hose 36. The security strap 24 is shown with the circular portion 44 encircling the adapter 14 on the proximal side of a typical flange 60 on the adapter 14. The arms 46 and 48 of the security strap are shown in tension and extending axially over the adapter flange 60 and the coupling 32, and through the slots 52 and 54 (FIGS. 2 and 3) of the connector flange 50. End abutments 40 and 42 are on the distal side of the fange 50 and are dimensioned so that they have a width substantially greater than the width of the slots 52 and 54 and cannot move axially through the slots. For example, in FIG. 5, the abutment 40 is shown against the distal side of flange 50 and extending beyond the opposed edges of slots 52. The elastic security member 24 is maintained in tension urging the adapter 14 and connector 22 toward each other. The adapter 14, connector 22, and elastic security member 24 thus provide a secure fluid connection arrangement connecting the tube 12 with the gas supply hose 36 for supplying gas to the lungs of the patient.

The security member 24 is quickly and simply applied and, when desired, readily removed from the adapter 14 and connector 22. For example, when applying the security member to the adapter 14, the circualr portion 44 of the security member 24 may be stretched and slipped over the coupling 32 of the adapter 14 and positioned just proximally of the adapter flange 60. The connector 22, which may be previously connected in fluid-tight, frictional engagement with tube 12 by means of coupler 28, is inserted into the adapter coupling 32 to urge coupler 30 into frictional, fluid-tight engagement with the walls 34 of the coupling. Then the security member abutments 40 and 42 are gasped and the arms 46 and 48 stretched axially until the abutments are distally beyond the connector flange 50 so that the arms 46 and 48 can be moved radially into the slots 52 and 54 of the flange 50. The arms 46 and 48 are forced into the slot entrances 56 and 58 and moved into the bottom portions of the slots. When it is desired to disconnect the adapter 14 from the connector 22, the abutments 40 and 42 are grasped and the arms manually moved radially outwardly until they are free of the slots 52 and 54. Then the connector 22 is forced from the adapter 14.

The closed loop 44 provides a simple and effective means of securing the security member 24 to adapter 14 or to adapters of other constructions where the loop can be positioned around a suitable part of the adapter. Also, the slotted flange 50 and the elastic arms 46 and 48 with the end enlargements 40 and 42 provide a simple and effective connection with the connector 22. The two tensioned arms 46 and 48 urge diametrically opposed portions of the flange 50 axially toward the adapter to provide a better balance of forces on the flange for a more stable strap arrangement, as compared to a case where only one arm is used. Since loop 44 encircles adapter 14, upon disconnection of the adapter 14 and connector 22, the security member 24 remains on the adapter and is not subject to loss.

FIG. 6 shows the medical connector device 10 in a fluid-tight connection with a conventional Y-adapter 60 of gas supply equipment. In such case, the elastomeric security member 24 may be conveniently placed between the legs 62 and 64 of the Y as shown, and the arms 46 and 48 then stretched and easily placed in the slots 52 and 54 of the connector 22. In this arrangement, the circular portion 44 does not itself encircle a portion of the adapter as is the case with the adapter 14 in FIG. 1.

The security strap 24 is a single part which may be molded of a soft, elastic material as previously mentioned herein. It may have an overall untensioned length of about 7 or 8 cm. The width, as viewed in FIG. 4, of the arms 46 and 48 and closed loop portion 44 may be about 5 mm. The thickness of the arms may be about 3.2 mm and the loop portion 44 and abutments 40 and 42 about 5 mm in thickness. The opening 45 of the loop portion may, for example, be circular when in its relaxed or untensioned state, as shown in FIG. 4, and have a diameter of about 16 mm. Also, in some cases, the security member may be provided with only one arm instead of the two shown, however, two arms, such as arms 46 and 48, generally provide a more effective security arrangement as pointed out above.

While two adapters 14 and 60 have been shown for purposes of illustration, the connector 22 and elastic security member 24 can be readily used with various other, differently shaped adapters.

The connector flange 50 in the preferred embodiment is provided with openings in the form of slots 52 which intersect or extend to the outer periphery of the flange and this allows easy insertion of the security strap 24 into holding engagement with the connector 22. However, if desired, one or more openings may be provided in the flange which do not extend to the periphery of the flange. For example, an opening(s) can be provided in the flange which is sized to allow a security strap abutment (40 or 42) to pass axially through it. In such case, the opening may have a relatively large portion for receiving the abutment and a relatively small portion into which the security strap arm is moved after insertion of the abutment. In this way, the small portion of the opening prevents the abutment from moving back through the opening. When disconnecting the security strap, the arm is moved back into the large portion of the opening to allow the strap abutment to pass back through the opening.

Also, while the security member or strap 24 is elastic in the preferred embodiment and can be stretched to fit various adapter couplings and provide a resilient force tending to hold the connector and adapter together, a non-elastic security strap or one having little elasticity may be used if desired.

As various changes could be made in the above construction without departing from the scope of the invention, it is intended that all matter contained in the above description or shown in the accompanying drawing shall be interpreted as illustrative and not in a limiting sense.

What is claimed is:

1. Medical fluid connection means for releasably connecting a tracheal tube adapted to be intubated in a patient to a fluid coupling adapter of gas supply equipment having slip-fit connection means comprising a single-piece connector having a bore therethrough and with the distal end thereof connectible with the proximal end of a tracheal tube to connect the tube in fluid communication with said bore, said connector having an integral slip-fit coupler at the proximal end thereof connectible with the slip-fit connection means for connecting the adapter in fluid communication with said bore and the tracheal tube, and radially extending flange means having a pair of diametrically disposed slots extending inwardly from the radially outer periphery thereof, each of said slots having a radially outer entrance portion of less width than an inner portion thereof, and an elastic security member having diametrically opposed free ends and an integral intermediate portion between said opposed free ends, said intermediate portion being capable in use of extending at least partially around a part of an adapter, said intermediate portion including a closed loop portion forming an opening adapted to encircle a portion of an adapter, and a pair of arms integral with and extending diametrically in opposite directions from said loop portion and integrally connected respectively to said free ends, each of said arms having a portion thereof movable into one of said slots and having a width greater than the width of said entrance portion of the slot, each of said free ends having a width greater than the width of said inner portion of each of said slots and the width of said portions of said arms and engageable with said flange means on the distal side thereof to hold the ends of the elastic member in place whereby said elastic member resiliently resists the fluid coupling adapter and said connector from moving apart when in use.

2. The connection means of claim 1 wherein said closed loop portion and said opening are generally circular for encircling a tubular portion of a fluid coupling adapter when used, and the width of said arms and said loop portion are approximately the same.

3. A tracheal tube assembly adapted to be connected to a fluid coupling adapter of gas supply equipment having slip-fit connection means comprising a tracheal tube having a distal end adapted to be inserted into a trachea of a patient, a single-piece connector having a bore therethrough and having the distal end thereof connected with the proximal end of said tracheal tube to connect said tube in fluid communication with said bore, a slip-fit coupler at the opposite end of the connector connectable with the slip-fit connection means for connecting the adapter in fluid communication with said bore and said tracheal tube, and radially extending flange means having a pair of diametrically disposed slots extending inwardly from the radially outer periphery thereof, each of said slots having an outer entrance portion of less width than an inner portion thereof, and an elastic security member having diametrically opposed free ends and an integral intermediate portion between said opposed free ends, said intermediate portion being capable in use of engaging and extending at least partially around a part of an adapter, said intermediate portion including a generally central closed loop portion forming an opening adapted to encircle a part of an adapter, and a pair of arms integral with and extending diametrically in opposite directions from said loop portion and integrally connected respectively to said free ends, each of said arms having a portion thereof movable into one of said slots and having a width greater than the width of said entrance portion of the slot, each of said free ends having a width greater than the width of said inner portion of each of said slots and the width of said portions of said arms and engageable with said flange means on the distal side thereof to hold the ends of the elastic member in place whereby said elastic member tends to resiliently urge the adapter and said connector toward each other in use.

* * * * *